United States Patent [19]
Leone et al.

[11] Patent Number: 5,885,244
[45] Date of Patent: Mar. 23, 1999

[54] SYNCHRONOUS, PULSATILE ANGIOPLASTY SYSTEM

[75] Inventors: James E. Leone; Eduardo deMarchena, both of Miami, Fla.

[73] Assignee: Cordis Corporation & University of Miami, Miami Lakes, Fla.

[21] Appl. No.: 856,349

[22] Filed: May 14, 1997

[51] Int. Cl.$^6$ .................................................. A61M 25/00
[52] U.S. Cl. .............................. 604/49; 604/96; 604/131; 606/194
[58] Field of Search .............................. 604/49, 96–100, 604/131–133, 151–154, 246–249; 606/192–194

[56] References Cited

U.S. PATENT DOCUMENTS

| | | |
|---|---|---|
| 3,099,260 | 7/1963 | Birtwell . |
| 3,266,487 | 8/1966 | Watkins et al. . |
| 3,428,042 | 2/1969 | Chestnut . |
| 3,447,479 | 6/1969 | Rosenberg . |
| 3,449,767 | 6/1969 | Bolie . |
| 3,456,444 | 7/1969 | Rishton . |
| 4,014,318 | 3/1977 | Dockum et al. . |
| 4,046,137 | 9/1977 | Curless et al. . |
| 4,284,073 | 8/1981 | Krause et al. . |
| 4,345,594 | 8/1982 | Bisera et al. . |
| 4,493,697 | 1/1985 | Krause et al. . |
| 5,066,282 | 11/1991 | Wijay et al. . |
| 5,486,192 | 1/1996 | Walinsky et al. . |

*Primary Examiner*—John D. Yasko
*Attorney, Agent, or Firm*—Lockwood, Alex, FitzGibbon & Cummings

[57] ABSTRACT

A synchronous, pulsatile angioplasty system utilizes a control apparatus which controls balloon inflation and deflation in a pulsatile fashion synchronized with the heartbeat of a patient. A heart monitor provides an input, a signal to the control apparatus which serves as a baseline for operation of the pulsatile inflation and deflation of the balloon. A triggering circuit reads the baseline signal and generates a control signal to selectively generate valves interconnecting the angioplasty catheter with sources of inflation media and low pressure. Time delay circuits may be utilized which delay either the duration of the control signal or the receipt thereof by the control valves.

24 Claims, 4 Drawing Sheets

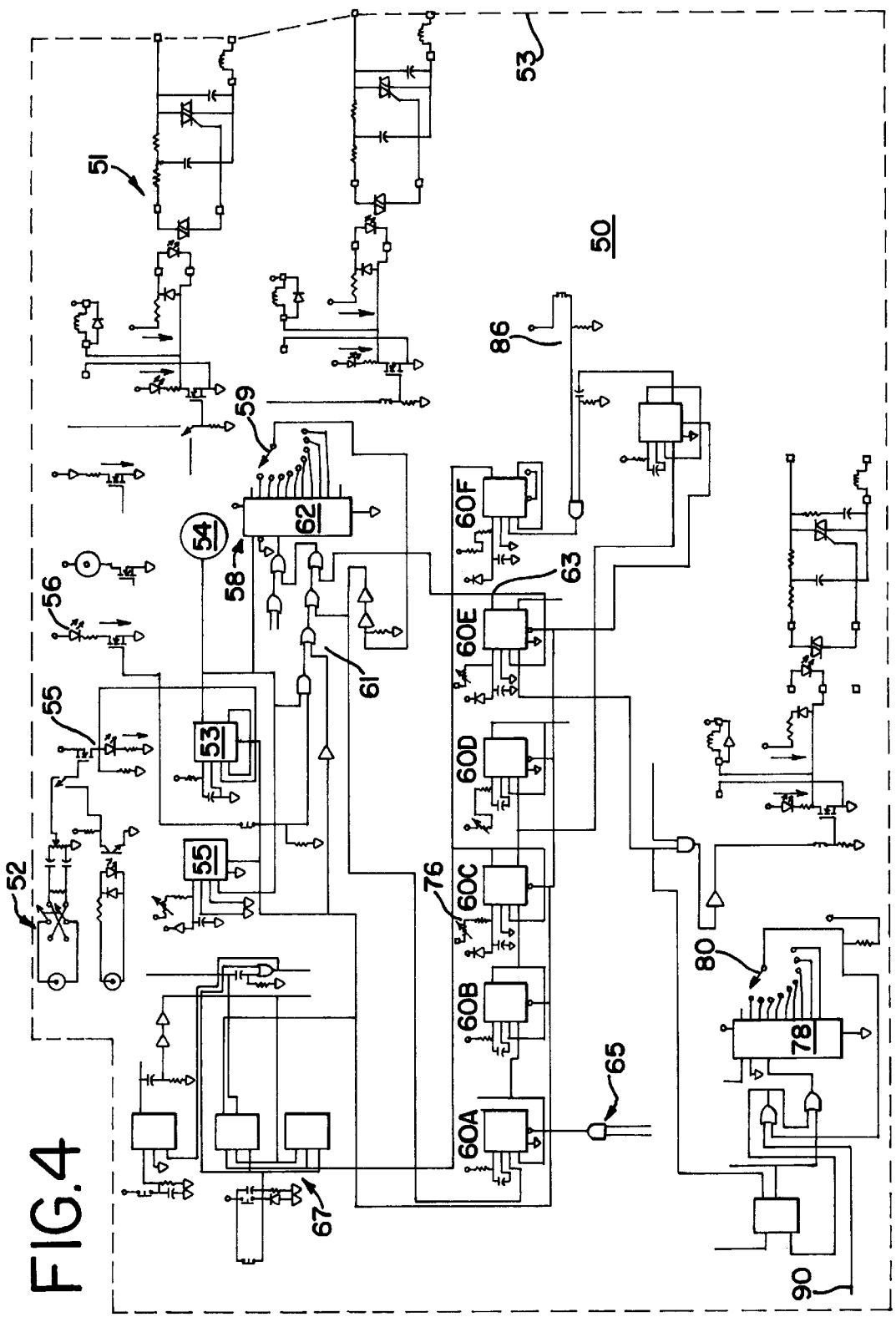

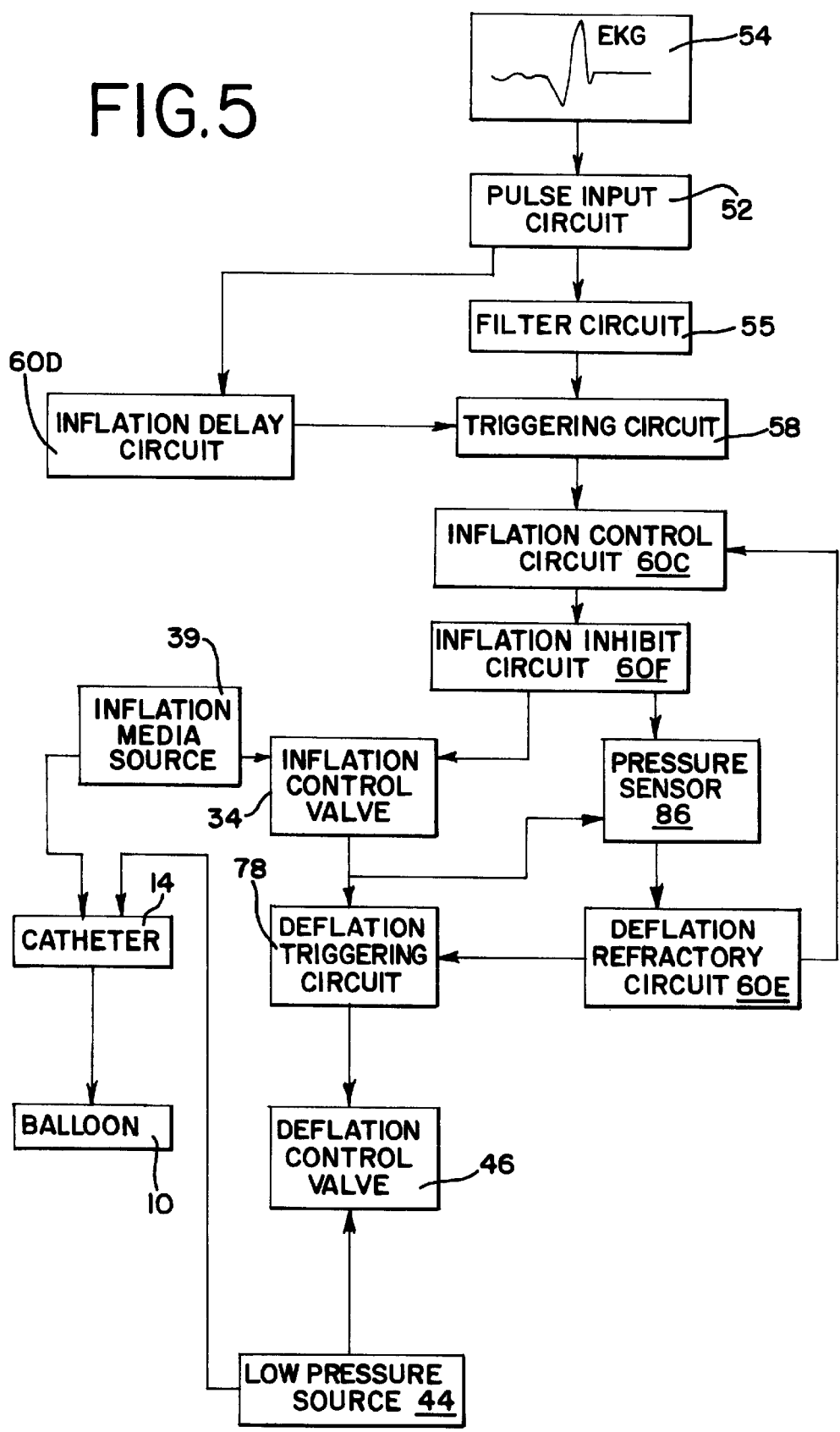

1

SYNCHRONOUS, PULSATILE ANGIOPLASTY SYSTEM

BACKGROUND AND SUMMARY OF THE INVENTION

The present invention relates generally to equipment and procedures employed in the performance of perfusion catherization procedures, and more particularly to a system for operating an angioplasty catheter in a pulsatile fashion in synchronization with a heartbeat.

The use of inflatable balloon catheters in the treatment of coronary conditions is widespread. Balloon catheters are commonly used to expand blockages in arteries. These blockages are a narrowing of an artery or other body vessel, and are referred to as stenoses. In angioplasty procedures, a guide catheter is introduced into the artery of the patient and guided through the artery until the distal tip of the catheter is at the desired location of the coronary artery near the stenosis. A dilation catheter having an inflatable balloon affixed to its distal end is introduced along the guide catheter and advanced into the patient until the balloon end is located at the stenosis. The balloon is subsequently inflated to expand it against the artery walls to expand, or dilate, the artery and compress the stenosis. This expansion can remove all of or a significant portion of the blockage when the balloon is inflated against the arterial walls for a preselected time or repeatedly inflated and deflated in a cycle to match that of the heartbeat of the patient.

Once the artery has been expanded, the balloon is deflated and it and the guide catheter are removed so that blood may again flow on its own through the artery. Restenosis is a condition where the arterial wall has been initially expanded by the balloon and the arterial blockage is open but the arterial wall contracts and adopts all of or part of its original, restricted state sometime after the balloon is deflated and removed. The rate of restenosis is believed to be lowered if longer inflation times are used during angioplasty balloon catheterization procedures.

The use of longer balloon inflation times may promote the occurrence of ischemia of the cardiac muscles. Ischemia is a local deficiency of oxygen in an area of the body caused by an obstruction in the blood vessels supplying blood to that area. To prevent ischemia, perfusion catheters are used in association with coronary angioplasty catheters. Perfusion catheters are catheters which permit the continuous flow of blood through the blockage during the inflation of the balloon in the artery.

An external pump is often used in perfusion angioplasty procedures in order to draw blood from the patient by way of an aspiration catheter and circulate it back through the perfusion catheter and past the distal end of the balloon. External blood pumps have been commonly used for regulating blood through coronary arteries during open-heart surgeries. These pumps may generally provide either a high or low pressure output. External perfusion pumps are well known, such as the one described in U.S. Pat. No. 5,066,282 issued Nov. 19, 1991. This patent is directed to a perfusion pump with a pulsation-damping mechanism that serves to smooth out pressure pulses of the pump during pumping. Other external pumps are known which use syringes as their primary components, such as that described in U.S. Pat. No. 3,447,479, issued Jun. 2, 1967 which discloses an arrangement of syringe pumps which perform alternating suction and pumping strokes. In the multiple syringe pump arrangement shown in this patent, four syringe pumps are powered by a motor-driven eccentric cam drive which utilizes return springs connected to the plungers of the syringe pumps in order to ensure a prompt return of the syringe pump plungers to their original, ready position within the syringes. The pumping cycle of such a mechanism is essentially "fixed" because of the curvature of the cam surfaces of the cam. It is not possible to adjust such a mechanical type system to mate its pumping action with a heartbeat.

The present invention is therefore directed to an angioplasty system with a control means for selectively controlling the inflation and deflation of an angioplasty balloon in synchronization with a patient's heartbeat in order to deflate the balloon while the heart is pumping and to inflate the balloon while the heart is at rest. The present invention therefore also dispenses with the need to utilize a perfusion catheter and its external perfusion pump.

In accordance with one aspect of the present invention, a heart monitor and a programmable controller are linked together so that the controller, in effect, "reads" the heart rate or pulse of the patient. The controller controls a bank, or a manifold, of valves that control the inflation and deflation of the angioplasty balloon using a biocompatible inflation media, such as helium or carbon dioxide. The valves are operatively connected to a pressurized source of inflation media as well as a vacuum source to provide for immediate inflation and deflation upon demand in response to a signal generated by the controller.

In another aspect of the present invention, a series of gas pressure regulators interconnect the pressurized inflation media source to a series of solenoid valves which are operatively connected to a programmable control means in order to regulate the pressure of the inflation fluid drawn from its source and used for balloon inflation purposes.

In yet another aspect of the present invention, the programmable controller has an adjustable control means with a timing delay means operatively associated therewith in order to adjust the frequency of the inflation and deflation cycles of the angioplasty balloon so that the balloon may be inflated and deflated in synchronization with the patient's heart so that angioplasty may be performed with minimal trauma and ischemia occurring. The timing delay means permits the programmable controller to synchronize the inflation of the balloon (and its deflation) not only to the heartbeat of the patient, but also in synchronization with a particular heartbeat, such as the fourth or sixth heartbeat, for example, in a chosen cycle.

Accordingly, it is a general object of the present invention to provide a pulsatile, synchronous inflation system for use in angioplasty which reduces trauma and ischemia.

Another object of the present invention is to provide a pulsatile angioplasty system wherein the balloon inflation pressure are adjustable and may be increased as required.

Still another object of the present invention is to provide an angioplasty inflation/deflation control system having a programmable controller which controls and regulates the inflation/deflation of an angioplasty balloon in synchronization with the heart rhythm of the patient, thereby permitting preselected longer or shorter periods of time of inflation during angioplasty and thereby reduces the trauma associated with angioplasty.

Yet another object of the present invention is to provide a synchronous, pulsatile angioplasty system having a control apparatus which synchronizes the inflation and deflation of an angioplasty balloon with the heartbeat of a patient and which controls the inflation and deflation times so that the angioplasty balloon may be inflated or deflated at every Nth heartbeat.

These and other objects, features and advantages of the present invention will be clearly understood through consideration of the following detailed description.

BRIEF DESCRIPTION OF THE DRAWINGS

In the course of the following detailed description reference will be frequently made to the accompanying drawings in which:

FIG. 3 is an end view of the inflation-deflation control apparatus represented by the diagram of FIG. 2 used in conjunction with the system of FIG. 1;

FIG. 4 is a schematic diagram illustrating the circuitry which is utilized in a preferred embodiment of the inflation-deflation control apparatus of FIG. 2; and, FIG. 5 is a schematic circuit logic chart illustrating the operation of the system of the invention and particularly, the inflation-deflation control apparatus thereof.

DETAILED DESCRIPTION OF THE PREFERRED EMBODIMENT

Figure 1:
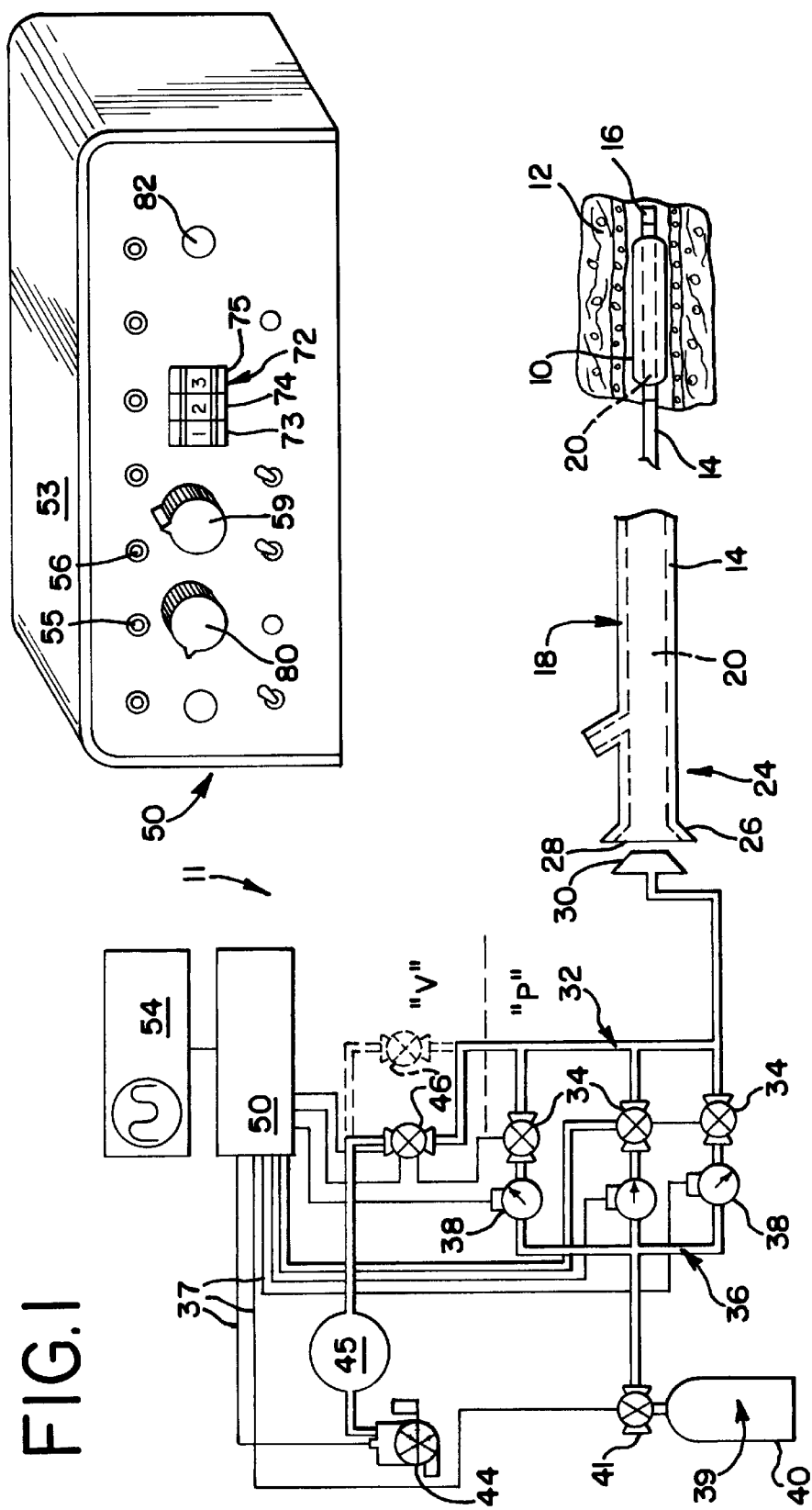
FIG. 1 is a simplified block diagram of a synchronous, pulsatile balloon angioplasty system constructed in accordance with the principles of the present invention.
Figure 2:
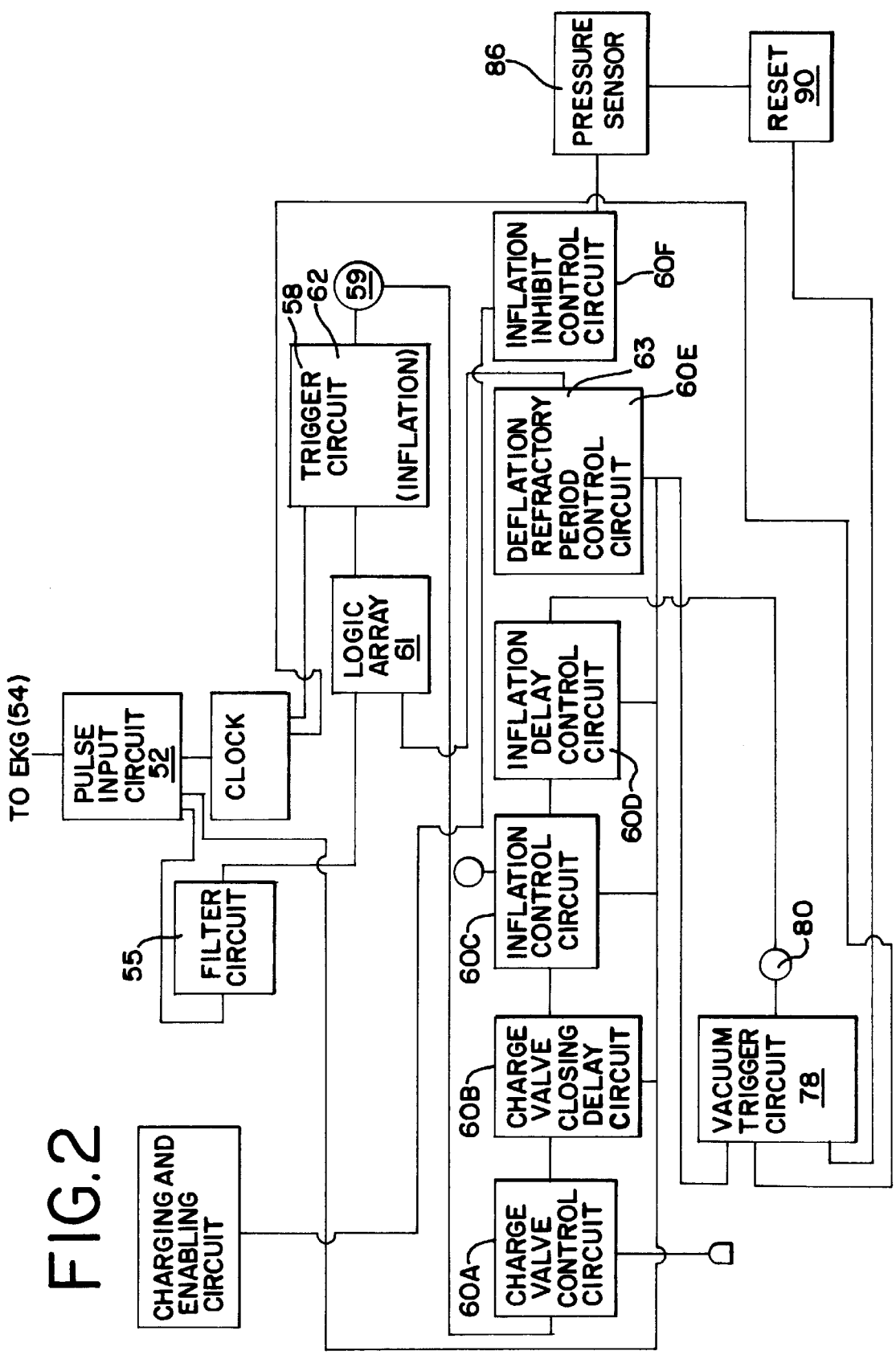
FIG. 2 is a functional block diagram of an inflation-deflation control apparatus utilized in the angioplasty system of FIG. 1.

FIG. 1 is a simplified block diagram of a synchronous, pulsatile angioplasty system contacted in accordance with the principles of the present invention. An angioplasty balloon, generally designated as 10, is illustrated in place within a blood vessel 12 of a patient. The angioplasty balloon 10 is mounted on an angioplasty catheter 14 at an insertion end 16 thereof. The catheter 14 includes an elongated shaft 18 having one or more internal lumens 20 extending therethrough in order to convey an inflation media to the balloon 10 when it is in place within the blood vessel 12.

The distal, or insertion end 16, of the catheter, carries the balloon 10 thereon in a normally deflated state so that it may be introduced into a blood vessel 12 such as a coronary artery in a conventional manner and positioned in place at a stenosis or otherwise occluded section of the blood vessel 12. The proximal end 24 of the catheter 14 extends out of the blood vessel 12 and the patient's body and is equipped with an inflation hub 26 which has an opening 28 therein that communicates with the internal inflation lumen 20 of the catheter 14. An appropriate connector 30, such as a luer connector, is used to connect the catheter inflation hub 26 to an inflation-deflation manifold 32, of valves 34 that are specifically used to control the inflation and deflation of the angioplasty balloon 10.

Focusing specifically now on the inflation-deflation manifold 32, it can be seen that the manifold bank 32 includes a plurality of inflation control valves 34, such as Skinner Model No. MDB005 mini-solenoid valves, in place on an equalizer assembly 36. The solenoid operators of those valves 34 are interconnected to an inflation-deflation control apparatus 50 by ways well-known in the art and in this regard, the valves 34 may be connected as at 37 to various circuits of the control apparatus 50.

Each regulating valve 34 has an inflation media regulator 38 associated therewith, preferably a gas pressure regulator, such as a Wilkerson R04-01-N00 non-relieving pressure regulator. These inflation media regulators are interposed between the regulating valves 34 and a pressurized inflation media supply 39 in order to control and vary (if desired) the inflation pressure of the media entering the inflatable balloon 10. The inflation media supply 39 is shown schematically as a pressurized tank 40, which has a charging valve 41 associated therewith which controls the flow of inflation-media out of the supply tank 40 and into the inflation-deflation manifold 32. The inflation media regulating valves 34 and the supply tank charging valve 41 are preferably linked in operative communication with the control apparatus 50 by circuitry 37 extending between the control apparatus 50 and the solenoids on the valves 34 and 41, and are further preferably all independently adjustable. The three pressure regulators 38 independently feed the inflation manifold through the three associated solenoid valves 34 which are ganged together as depicted on the pressure side "P" of the system.

A vacuum assembly 40 is also interconnected to the manifold 42 and includes a source of low pressure disposed on the vacuum side "V" of the system, such as the vacuum pump 44 and a ballast or holding tank 45, illustrated. This vacuum line also includes a control valve 46, preferably in the form of a solenoid operated valve as described above for the inflation control valves 34 of the pressure bank 32. Two such valves 46 may be used in conjunction with a vacuum portion of the manifold 32 so that three valves 34 are dedicated to the pressure made of the system, while two such valves 46 are dedicated to the vacuum side of the system.

The solenoids that operate these valves 34, 46 are timed by the controller 50 and may be operated by a time-delay circuit thereof as explained below. The vacuum valves 46 are also preferably operatively connected to the control apparatus 50. The inflation media used for inflating the balloon 10 may be a biocompatible liquid, such as a saline solution, or as used in the preferred embodiment of the present invention, it may be a biocompatible gas, such as helium or carbon dioxide, both of which are inert with respect to body tissues and which are readily absorbed by body tissues.

As will become evident from further reading of this detailed description, the ballast tank 45, when a vacuum is maintained on it, importantly provides a means for collecting the inflation media from the catheter 14 during balloon deflation, thereby providing rapid deflation with any range of inflation times. This rapid deflation is effected by a signal from the controller 50 which is used to control the sequence and timing of inflation and deflation of the angioplasty balloon 10.

Focusing now on FIG. 4, the circuitry 51 of the control apparatus 50 is shown schematically. The circuitry 51 is contained within an apparatus housing 53 as shown in FIG. 3, and it includes an input circuit 52 which receives the pulse from a heart monitoring system, such as an EKG 54 and provides a means for monitoring the heartbeat of a patient and a baseline pattern for use with the control apparatus 50. The control apparatus receives a QRS signal from the EKG monitor 54 applied to the patient. This signal is passed through a TTL (transistor-transistor logic) input portion of the input circuit 51 and also may also be passed through a filter circuit 55 in order to screen undesirable "noise" received in conjunction with the input from the EKG monitor 54.

Means for visually observing the heartbeat, as well as the synchronization of the balloon inflation and deflation with the heartbeat may be provided in the form of one or more external LEDs ("light-emitting diodes") mounted on the panel in positions which are easily visible by the operator.

One such LED is associated with the heartbeat, or pulse of the patient that is received as an input to the control apparatus 50 and is indicated at 56. This LED 56 flashes in synchronization with the pulse input of the patient so that the operator of the control apparatus can easily visually observe it.

Once the heartbeat or pulse of the patient has been established, that baseline signal is sent from the input circuit 52 to a triggering circuit 58 which provides the operator of the control apparatus 50 with a means of selecting a desired synchronization of the operation of the system, i.e., a pulsatile inflation and deflation of the angioplasty balloon 10 with the heartbeat of the patient or with a particular synchronized heartbeat cycle thereof. This cycle may be synchronized to the patient heartbeat input by means of a filter circuit 55 in a one-to-one relationship where the balloon 10 is inflated and deflated successively with respect to every systolic and diastolic beat of the heart.

More uniquely, it may be synchronized by the filter circuit 55 to a particular heartbeat, N, so that the system may inflate the balloon every Nth heartbeat while it deflates the balloon 10 and maintains it in a deflated state for the intervening heartbeats. For example, when the N value is chosen to be 4, the control apparatus 50 will by way of its input circuit 52 count the heartbeats received from a patient and every fourth heartbeat, the triggering circuit 58 will send a signal to open the charging valve 41 and/or the inflation control valves 34 to inflate the balloon 10 for a particular predetermined time simultaneously with that Nth (fourth) heartbeat, while deflating it upon receipt of a signal from the heartrate input circuit 52 indicating the end of the Nth (fourth) heartbeat. Similarly, the triggering signal may be sent to initiate an inflation of the balloon 10 for a time longer than just a heartbeat, such as a 2-second time period to promote an intermittent, but steady inflation against the stenoses of the blood vessel 12.

Returning now to the schematic diagram, FIG. 3, a triggering circuit 58 is shown as interconnected to a series of control circuits 60 A–F which may be considered as primarily timing circuits in that for the most part, they rely upon an elapsed time before actuating their associated control valves and/or regulators. One such control circuit 60A operates the charging valve 39 in a selective fashion in order to fill, or charge, the inflation manifold with inflation media under pressure. The triggering circuit 58 receives both the input signal from the EKG 54 and also a signal from an array of logic gates 59 into which signals are fed from selected control circuits 60 A–F, as well as the heartbeat input signal from the input circuit 52. The various inputs received in the triggering circuit processor 62 are analyzed and a triggering control signal is generated. This signal is received by the charging valve, or inflation, circuit 60A which controls the operation (i.e., opening and closing) of the charging valve 41 of the pressurized supply 40 of inflation media. The triggering circuit 58 may be set to trigger an inflation of the balloon with a specific heartbeat by way of a rotary selector switch 59.

Upon opening of the charging valve 41, the output of this charge valve control circuit 60A is received by a charge valve closing time delay circuit 60B which may be set to delay closing of the charging valve 41 for a predetermined time in order to keep it open for the desired inflation period. An inflation control circuit 60C receives a control signal as output from the charge valve delay circuit 60B and also receives as input, the heartbeat signal in order to control operation of the inflation control valves 34 when the triggering signal from the triggering circuit 58 and the heartbeat input signal match.

An inflation valve closure delay control circuit is provided at 60D in order to maintain the inflation control valves 34 in an open position for a preselected amount of time as set by a potentiometer 76 as described in detail below. One output of this control circuit 60D leads to a vacuum triggering circuit 78 which generates a signal from its processor to trigger operation of the low pressure control valve 46. The vacuum triggering circuit 78 may include a rotary selector switch 80 for selecting a predetermined delay in operating the deflation control valve(s) 46. This is used in instances where the operator desires to deflate the balloon 10 after a desired number of pulses rather than immediately after the inflation of the balloon 10. The rotary selector switch 80 of this circuit 78 permits the deflation to be delayed in predetermined incremental values, such as an Nth heartbeat, up to a maximum of 9 heartbeats.

The control apparatus 50 further includes a control circuit 60E which serves to ensure that the inflatable balloon 10 is fully deflated before any new event (i.e. another inflation) is processed. One output 82 of this circuit 60E is processed through the logic array 59 and is received by the triggering circuit processor 62 where it is read and accepted in order not to transmit another triggering signal until balloon deflation is completed.

Lastly, the control circuits also include an inflation inhibiting circuit 60F serves as a balloon overpressure and rupture alarm. This circuit receives as input, a signal from a pressure sensor 86 preferably positioned in line with the catheter luer connector 30 and triggers an alarm circuit 88 which resets the control apparatus cycle and stopping the inflation cycle by closing the charging valve 41.

The triggering circuit 58 is connected to a rotary selector switch 59 accessible from the front panel of the apparatus 50. This selector switch 59 selects the desired number of "N" detected heartbeats, or pulses, required to trigger an event. Presently, suitable results have been obtained using the control apparatus with a maximum limit of 9 heartbeats or pulses. An inflation timing control switch 72 extends through the front panel of the control apparatus and may be located next to the trigger selector switch 59. This control switch 72 preferably takes the form of a digital potentiometer 76 with three incremental selectors 73, 74, 75 being arranged thereon. This potentiometer has the ability to permit the operator to select inflation times of the balloon 10 up to 5 seconds. The time is set by choosing the proper incremental valves on the control switch 72 ranging from between the baseline setting of 25 milliseconds when the switch 59 reads "000" on all these dials thereof and up to the 5 second maximum. The increments are effected by turning the rightmost indicator 75 to obtain a number in the display of between 0 and 9, each number representing an integer multiplier of the base value of 5 msec. The center indicator 74 results in an increase of 50 msec, while the leftmost indicator 73 results in an increase in the inflation time of the balloon of 500 msec for each digit. As an example, a setting of "123" on the switch 72 yields a total inflation time of 500 msec as shown below:

Time T=(1×500 msec)+(2×50 msec)+(3×5 msec)+baseline valve of 25 msec.=640 msec.

The control apparatus 50 may be provided with a reset control switch 90 which will stop all of the functions of the control apparatus by turning off all controls to the inflation valves 36 and resetting all of the counters of the control apparatus, yet maintaining the vacuum valve(s) 46 enabled and opened to provide continued deflation.

The control apparatus 50 also preferably includes inhibit circuits which prevent the pressure side P of the system from operating while the vacuum side V is operating. A delay is programmed into the inflation valve circuits through the inflation delay control circuit 60D in order to account for the time it takes for the inflation control valves 34 to mechanically close before triggering the vacuum circuit 78. This feature is important because if the pressure side P is open at the same time the vacuum side V is, the vacuum side will become burdened with the pressure and it will take time for the vacuum side to be drawn back down to the required vacuum level. The deflation control period circuit 60E which controls the vacuum valve(s) 46 inhibits any events from initiating before the deflation has run out in order to obtain complete deflation of the balloon 10.

FIG. 5 is a schematic circuit logic diagram that describes the sequence of operation of the system of the present invention. As shown in FIG. 5, the heart monitor, EKG 54, reads the heartbeat, or pulse, of the patient. The pulse input circuit 52 is adjustable to set a predetermined threshold or baseline value. Any pulses received from the monitor 54 above this threshold or baseline are received by the pulse input circuit 52 and identified as a "valid" pulse to the control apparatus. This pulse is then passed through the filter circuit 55 which is an adjustable event filter that can be selectively adjusted to provide a particular sequence, i.e. it passes every pulse, every other pulse, every Nth pulse, etc.

The selected sequence of the event filter 55 is communicated the trigger delay circuit 62 which activates an inflation solenoid valve 34 that is connected to a high pressure gas reservoir that serves as the inflation media supply 39. The inflation solenoid valve 34 is activated after a selected delay time applied to receiving the appropriate signal(s) from the circuits 60A, 60B, 60C, and 60D. The vacuum trigger circuit 78 serves as a deflation trigger circuit to deflate the balloon 10 by opening the deflation solenoid valve 45 either immediately after inflation of the balloon 10 or after a selected number N of pulses.

The deflation refractory circuit 60E overrides any inflation signal from activating the inflation valve 34 until the balloon 10 is fully deflated, normally 500 to 800 milliseconds, and this circuit 60E further holds the deflation solenoid valve 45 open to vacuum until an inflation signal is received by the inflation trigger circuit 62. Various "failsafe" features are included as part of the inflation inhibit circuit 60F which serve to control the inflation valve 34 and prevent it from operating in the event of the balloon 10 or the catheter body 14 bursting or leaking.

In brief, the present invention takes as input, a heartbeat or pulse output, from a suitable heart or blood pressure monitor and correlates the inflation and deflation cycles of the controller to the heartbeat input. This signal provides the control apparatus with a baseline signal for operation so that the balloon may be inflated at particular heartbeats. Rather than merely delaying the inflation for a preselected time interval after detecting a pulse signal, the present invention correlates the pulses to the balloon so that it may be inflated and deflated in synchronization with a desired Nth pulse or heartbeat. Once inflated, the balloon may be deflated by the operator either immediately after inflation or after a preselected number of pulses read by the input.

While the preferred embodiment of the invention have been shown and described, it will be apparent to those skilled in the art that changes and modifications may be made therein without departing from the spirit of the invention, the scope of which is defined by the appended claims.

We claim:

1. A method for performing synchronous, pulsatile angioplasty on a patient, comprising the steps of:

providing an angioplasty balloon catheter having an elongated shaft, an inflatable balloon disposed on said shaft at a distal end thereof, and an inflation lumen extending lengthwise along said shaft, the inflation lumen having an inflation opening disposed at the catheter shaft distal end and communicating with said balloon, the inflation lumen further having an inflation media opening at a proximal end of said catheter shaft;

inserting said angioplasty balloon catheter into a blood vessel of the patient and positioning said balloon catheter into a predesired location within the blood vessel;

providing a source of inflation media, a source of low pressure and an inflation-deflation control apparatus;

operatively interconnecting said angioplasty balloon catheter, the inflation media source, the low pressure source and the inflation-deflation control apparatus together;

providing means for monitoring a heart rate of said patient and for generating a signal indicative of the heart rate of said patient;

generating a triggering signal within said inflation-deflation control apparatus in response to the heart rate signal by said heart rate monitoring means; and inflating and deflating said inflatable balloon in a cyclical, pulsatile pattern in response to said triggering signal received by said inflation-deflation control apparatus in synchronization with a particular heartbeat of said heart rate signal by alternatingly introducing said inflation media into said inflatable balloon from said inflation media source and evacuating said inflation media from said inflatable balloon.

2. The angioplasty method according to claim 1, further including the steps of:

interposing a manifold between said inflation media and low pressure sources and said inflatable balloon, the manifold having respective control valves associated therewith, and operating the control valves in response to the triggering signal in order to alternatively open and close said control valves to achieve said alternating inflation and deflation of said inflatable balloon.

3. The angioplasty method according to claim 2, further include the step of providing pressure regulating means for regulating inflation pressure of said inflation media entering said inflatable balloon.

4. The angioplasty method according to claim 3, wherein said inflation pressure regulating means is operatively connected to said heart rate monitoring means, said inflation media pressure regulating means being responsive to signals generated by said heart rate monitoring means to thereby regulate inflation pressure of said inflatable balloon.

5. The angioplasty method according to claim 1, further including the steps of:

providing counting means for counting the number of heartbeats of the patient in response to the signal from said heart rate monitoring means for a preselected time period;

selecting a particular number N of heart beats; and, generating said triggering signal in response to a heart rate signal to coincide with every Nth heartbeat signal received from said heart rate monitoring means to thereby inflate said balloon in synchronization with said Nth heartbeat.

6. The angioplasty method according to claim 4, further including means for inhibiting inflation of said inflatable balloon, the inflation inhibiting means being operatively connected to said inflation media pressure regulating means.

7. The angioplasty method according to claim 1, further including the steps of monitoring pressure of said inflation media entering said inflatable balloon to determine the integrity of said inflatable balloon and said balloon catheter.

8. The angioplasty method according to claim 7, further including means for inhibiting the generating of said triggering signal if the pressure of said inflation media entering said balloon catheter and inflatable balloon exceeds a predetermined value.

9. The angioplasty method according to claim 5, wherein said heartbeat counting means includes a filter circuit that receives said heart rate signal from said heart rate monitoring means, said filter circuit being selectively adjustable for selecting said heart beat number N.

10. The angioplasty method according to claim 1, further including means for counting time intervals between receipt of said triggering signal by said inflation-deflation control apparatus and the additional step of delaying inflating said inflatable balloon until after a preselected time interval has passed.

11. The angioplasty method according to claim 2, wherein said source of pressure is a vacuum source.

12. The angioplasty method according to claim 2, further including means for counting the number of heartbeats received from said heart rate signal, an inflation control valve and a deflation control valve, the inflation control valve being interposed between said inflation media source and said inflatable balloon and the deflation control valve being interposed between said low pressure source and said inflatable balloon, means for generating a deflation triggering signal, said inflation control valve being activated by said triggering signal to introduce said inflation media into said inflatable balloon and said deflation control valve being activated by said deflation triggering signal after a preselected number of heartbeats.

13. An angioplasty apparatus for inflating and deflating an inflatable balloon inserted into a blood vessel of a patient in a pulsatile manner in synchronization with the heart rate of the patient, the angioplasty apparatus comprising:

an angioplasty catheter having an elongated catheter shaft, an inflatable balloon disposed on the catheter shaft at a distal end thereof, an inflation lumen extending along said catheter shaft having an outlet at said catheter shaft distal end in communication with said inflatable balloon and an opposite inlet at a proximal end of said catheter shaft;

a pressurized supply of inflation media;

a low pressure supply;

an inflation-deflation media conveyance network interconnecting said proximal end of said catheter to said inflation media and low pressure supplies;

control valves disposed within said network and interposed between said catheter lumen inlet and said inflation media and low pressure supplies for selectively controlling flow of pressurized inflation media and low pressure in an alternating fashion through said network and into said catheter shaft lumen inlet in order to selectively inflate and deflate said inflatable balloon within the patient's blood vessel;

means for monitoring the heartbeat of the patient and for providing an input signal indicative of said heartbeat;

control means for activating said control valves in synchronization with said heartbeat input signal and alternatingly introducing and evacuating said pressurized inflation media into and from said catheter shaft lumen inlet to selectively inflate and deflate said inflatable balloon in synchronization with said heartbeat signal.

14. The angioplasty apparatus of claim 13, further including means for counting a preselected number N of heartbeats, said heartbeat counting means sending a control signal to said control means every Nth heartbeat to thereby generate a control valve triggering signal for inflating said balloon every Nth heartbeat.

15. The angioplasty apparatus of claim 13, wherein said inflation-deflation network includes an inflation pressure manifold and a low pressure manifold, at least one inflation control valve interposed in the inflation pressure manifold and operatively connected to said control means and at least one deflation control valve interposed in the low pressure manifold and operatively connected to said control means.

16. The angioplasty apparatus of claim 13, wherein said low pressure supply includes a vacuum source.

17. The angioplasty apparatus of claim 16, wherein said vacuum source includes a vacuum pump.

18. The angioplasty apparatus of claim 13, further including a plurality of pressure regulators operatively connected to said control valves and to said control means.

19. The angioplasty apparatus of claim 18, wherein said pressure regulators are responsive to said control valve triggering signals.

20. The angioplasty apparatus of claim 18, wherein said pressure regulators are interposed in said network between said inflation media supply and said control valves.

21. The angioplasty apparatus of claim 14, wherein said counting means control signal is received by said control means and generates a triggering signal every Nth heartbeat which triggers deflation of said balloon.

22. The angioplasty apparatus of claim 13, further including means for selectively filtering said heartbeat input signal to generate filtered heartbeat input signals above a preselected baseline and means for counting a predetermined number N of filtered heartbeat input signals, and generating a count signal every Nth filtered heartbeat, said count signal being received by said control means which thereupon generates a first control valve triggering signal which activates an inflation control valve to introduce said pressurized inflation media into said catheter in order to inflate said inflatable balloon every Nth filtered heartbeat.

23. The angioplasty apparatus of claim 22, further including means for generating a second control valve that connects said low pressure source to said catheter and evacuates said pressurized inflation media from said catheter in order to deflate said inflatable balloon after inflation thereof.

24. The angioplasty apparatus of claim 23, further including means for delaying deflation of said inflatable balloon for a predetermined time interval after inflation of said balloon.

* * * * *